United States Patent [19]
Klokkers et al.

[11] Patent Number: 6,165,498
[45] Date of Patent: Dec. 26, 2000

[54] TRANSDERMAL PREPARATION CONTAINING A LORATIDINE METABOLITE WITH ANTIHISTAMINIC ACTIVITY

[75] Inventors: Karin Klokkers; Wilfried Fischer, both of Lenggries; Daniel Bracher, Munich, all of Germany

[73] Assignee: Hexal AG, Holzkirchen, Germany

[21] Appl. No.: 08/849,206

[22] PCT Filed: Dec. 4, 1995

[86] PCT No.: PCT/EP95/04761

§ 371 Date: Mar. 23, 1998

§ 102(e) Date: Mar. 23, 1998

[87] PCT Pub. No.: WO96/16641

PCT Pub. Date: Jun. 6, 1996

[30] Foreign Application Priority Data

Dec. 2, 1994 [DE] Germany ............... 44 42 999

[51] Int. Cl.⁷ .................................................. A61K 9/70
[52] U.S. Cl. ......................................... 424/448; 424/449
[58] Field of Search ..................................... 424/448, 449

[56] References Cited

U.S. PATENT DOCUMENTS

| | | | |
|---|---|---|---|
| 4,910,205 | 3/1990 | Kogan et al. | 514/290 |
| 5,364,628 | 11/1994 | Kissel et al. | 424/448 |
| 5,656,286 | 8/1997 | Miranda | 424/449 |

FOREIGN PATENT DOCUMENTS 2098865  12/1982  United Kingdom.

OTHER PUBLICATIONS

"HPLC–Bestimmung von Loratadin und seinem aktiven Metaboliten Descarboethoxyloratadin in Humanplasma", Pharmazie 49 (1994), H. 10, pp. 736–739.

"Focus on Loratadin: A new second–generation nonsedating $H_1$–receptor antagonist", Hospital Formulary, Feb. 1993, vol. 28, No. 2, pp. 137–153.

*Primary Examiner*—Raj Bawa
*Attorney, Agent, or Firm*—Brooks & Kushman P.C.

[57] ABSTRACT

A transdermal patch contains an active loratidine metabolite contained with a polyacrylate polymer matrix. The transdermal patch provides pharmaceutically useful transdermal flux rates over time.

6 Claims, No Drawings

TRANSDERMAL PREPARATION CONTAINING A LORATIDINE METABOLITE WITH ANTIHISTAMINIC ACTIVITY

BACKGROUND OF THE INVENTION

1. Field of the Invention

The invention relates to a pharmaceutical composition for systemic transdermal administration comprising an active loratidine metabolite as active ingredient.

2. Description of the Related Art

Loratidine (ethyl-[4-(8-chloro-6,11-dihydro-5H-benzo[5,6]cyclohepta[1,2-b]pyridin-11-ylidene)-1-piperidinecarboxylate]) is an antihistamine that is available commercially as syrup or in the form of tablets. The active ingredient is metabolised in the body.

There is now a need to improve the antihistaminic effect and to provide a systemic form of administration. In tests carried out for that purpose, it has, surprisingly, been established that an active loratidine metabolite has sufficient stability to be provided as active ingredient in a pharmaceutical composition for systemic transdermal administration.

DETAILED DESCRIPTION OF THE INVENTION

The problem underlying the invention is solved by a pharmaceutical composition for systemic transdermal administration that comprises an active loratidine metabolite as active ingredient. The antihistaminic effect of the active loratidine metabolite can be exploited for that pharmaceutical composition.

A loratidine metabolite can be obtained from Irotec Laboratories (County Cork, Ireland) and has the following formula:

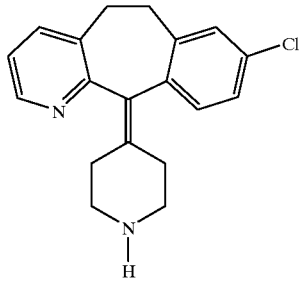

According to the invention, the pharmaceutical composition can be provided in the form of a customary liquid or solid form of systemic transdermal administration. For the relevant prior art, see, for example, DE-A-3 212 053, GB-A-2 098 865, Remington's Pharmaceutical Sciences, 16th edition, Mack-Verlag, and Sucker, Fuchs & Spieser, Pharmazeutische Technologie, 1st edition, Springer-Verlag.

The pharmaceutical composition according to the invention is customarily in the form of a viscous liquid, an ointment, a composition having a reservoir or a composition having a matrix. For example, the active loratidine metabolite may be present in a reservoir or matrix which are provided in the form of a gel or a polymer, for example in the form of a polymer according to EP-A-0 155 229.

According to a special embodiment, the pharmaceutical composition according to the invention may have a transdermal patch structure.

According to the invention, the patch structure can be provided by an acrylate-based matrix formed in customary manner on a carrier layer that is impermeable to water, it being possible to provide additionally a removable cover layer that protects the matrix.

According to the invention, the material of the matrix may be a non-swellable acrylate polymer, for example Durotack 280-2416 (Delft National Chemie, Zotphen, Netherlands).

The invention is explained hereinafter in greater detail by way of example.

In vitro test

A diffusion test is carried out in vitro according to Franz in J. Invest. Dermatol., 64 (1975) 194–195 and GB-A-2 098 865. For the test, the active loratidine metabolite is applied to one side of an isolated intact segment of mouse skin having a surface area of 2.5 cm$^2$. The other side of the skin segment is placed in contact with a 0.9% sodium chloride solution additionally containing 0.05% sodium azide. The amount of active ingredient that passes into the salt solution is monitored in customary manner by HPLC (HP Liquid Chromatography). Details are given below.

| Active loratidine metabolite 16.6 mg/ml propylene glycol: water (1:1) 5.0 ml Penetration rates per 2.5 cm$^2$ | | |
|---|---|---|
| time [h] | amount [μg/cm$^2$] | flow rate [μg/cm$^2$/24 h] |
| 3 | 9.0 | 72 |
| 6 | 85.1 | 341 |
| 9 | 175.2 | 467 |
| 14 | 333.6 | 572 |
| 19 | 508.3 | 642 |
| 24 | 578.8 | 579 |
| 32 | 884.2 | 663 |

EXAMPLE 1

There is provided a transdermal therapeutic system of the reservoir type. For that purpose, a cover foil of 15 μm thick polyester material is used which may be provided with a skin-coloured coating or may be transparent. The cover foil is heat-moulded onto a laminate that consists of a microporous membrane, a self-adhesive contact adhesive from the group of acrylates, silicones and polyisobutylene with a tackifying resin, and a protective foil. The microporous membrane may be of the MSX 115 4P type and may contain 28% EVA (ethylene vinyl acetate). The protective foil may be a polyester material, siliconised on one side, of 100 μm layer thickness. A cavity is left between the cover foil and the microporous membrane, which is filled with a saturated solution of the loratidine metabolite in a propylene glycol/water mixture (1:1).

EXAMPLE 2

| | |
|---|---|
| Loratidine metabolite | 2.0 g |
| Duro-Tak 1753 | 98.0 g |

The above-mentioned starting materials are mixed to form a clear solution. The solution is applied to a siliconised foil or paper to produce a content per surface area of 100 g/m$^2$. A transparent polypropylene or polyester foil is laminated onto the dried matrix. The finished patches are punched out of the laminate in sizes of from 10 cm² (corresponding to 2 mg of active ingredient) to 40 cm² (corresponding to 8 mg of active ingredient).

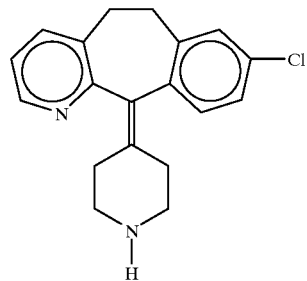

What is claimed is:

1. A process for the manufacture of a transdermal patch having a polymer matrix containing an active ingredient therein and suitable for systemic transdermal administration, whereas the improvement comprises selecting as said polymer matrix consisting essentially of an acrylate polymer and said active loratidine metabolite.

2. A pharmaceutical composition for systemic transdermal administration containing an active loratidine metabolite as an antihistamine, said pharmaceutical composition having a transdermal patch structure consisting essentially of an acrylate polymer and said active loratidine metabolite.

3. The process of claim 1 wherein said acrylate polymer is a non-swellable acrylate polymer.

4. A process for administering an antihistamine to a patient in need thereof, said process comprising contacting the skin of the patient with the transdermal patch of claim 2.

5. The pharmaceutical composition of claim 2 wherein said acrylate polymer is a non-swellable acrylate polymer.

6. The pharmaceutical composition of claim 2 wherein said loratidine metabolite has the structure